US00PP29182P2

(12) United States Plant Patent
Rijk

(10) Patent No.: US PP29,182 P2
(45) Date of Patent: Apr. 3, 2018

(54) ***BEGONIA* PLANT NAMED 'FIBEGMISSMAL'**

(50) Latin Name: *Begonia hybrida*
Varietal Denomination: Fibegmissmal

(71) Applicant: FIDES B.V., De Lier (NL)

(72) Inventor: Nadine Rijk, De Lier (NL)

(73) Assignee: Dümmen Group B.V., De Lier (NL)

( * ) Notice: Subject to any disclaimer, the term of this patent is extended or adjusted under 35 U.S.C. 154(b) by 0 days.

(21) Appl. No.: 15/330,931

(22) Filed: Nov. 15, 2016

(51) Int. Cl.
*A01H 5/02* (2006.01)

(52) U.S. Cl.
USPC ..... Plt./343

(58) Field of Classification Search
USPC ..... Plt./263.1, 343
See application file for complete search history.

*Primary Examiner* — Susan McCormick Ewoldt
*Assistant Examiner* — Karen M Redden
(74) *Attorney, Agent, or Firm* — C. A. Whealy

(57) ABSTRACT

A new and distinct cultivar of *Begonia* plant named 'Fibegmissmal', characterized by its upright to spreading and mounded plant habit; relatively compact; moderately vigorous to vigorous growth habit; freely basal branching habit; dark green-colored leaves; freely and continuously flowering habit; and large single female flowers that are pinkish red in color and large double male flowers that are orangish red in color.

1 Drawing Sheet

Botanical designation: *Begonia hybrida.*
Cultivar denomination: 'FIBEGMISSMAL'.

BACKGROUND OF THE INVENTION

The present invention relates to a new and distinct cultivar of *Begonia* plant, botanically known as *Begonia hybrida*, and hereinafter referred to by the name 'Fibegmissmal'.

The new *Begonia* plant is a product of a planned breeding program conducted by the Inventor in Rheinberg, Germany and De Lier, The Netherlands. The objective of the breeding program was to develop new freely branching and flowering *Begonia* plants with unique and attractive flower colors.

The new *Begonia* plant is a naturally-occurring whole plant mutation of *Begonia hybrida* 'Fimissmo', disclosed in U.S. Plant Pat. No. 27,484. The new *Begonia* plant was discovered and selected by the Inventor as a single flowering plant from within a population of plants of 'Fimissmo' in a controlled greenhouse environment in Rheinberg, Germany on Apr. 17, 2015.

Asexual reproduction of the new *Begonia* plant by vegetative tip cuttings in a controlled greenhouse environment in De Lier, The Netherlands since May 17, 2015 has shown that the unique features of this new *Begonia* plant are stable and reproduced true to type in successive generations.

SUMMARY OF THE INVENTION

Plants of the new *Begonia* have not been observed under all possible combinations of environmental conditions and cultural practices. The phenotype may vary somewhat with variations in environment such as temperature and light intensity, without, however, any variance in genotype.

The following traits have been repeatedly observed and are determined to be the unique characteristics of 'Fibegmissmal'. These characteristics in combination distinguish 'Fibegmissmal' as a new and distinct *Begonia* plant:

1. Upright to spreading and mounded plant habit; relatively compact.
2. Moderately vigorous to vigorous growth habit.
3. Freely basal branching habit.
4. Dark green-colored leaves.
5. Freely and continuously flowering habit.
6. Large single female flowers that are pinkish red in color and large double male flowers that are orangish red in color.

Plants of the new *Begonia* can be compared to plants of the mutation parent, 'Fimissmo'. In side-by-side comparisons, plants of the new *Begonia* differ primarily from plants of 'Fimissmo' in the following characteristics:

1. Plants of the new *Begonia* are shorter and broader than plants of 'Fimissmo'.
2. Plants of the new *Begonia* have larger leaves than plants of 'Fimissmo'.
3. Plants of the new *Begonia* and 'Fimissmo' differ in flower color as plants of 'Fimissmo' have cream-colored flowers with light pink-colored margins.

Plants of the new *Begonia* can be compared to plants of *Begonia hybrida* 'Fiunupfimp', disclosed in U.S. Plant Pat. No. 27,483. In side-by-side comparisons, plants of the new *Begonia* differ primarily from plants of 'Fiunupfimp' in the following characteristics:

1. Plants of the new *Begonia* and 'Fiunupfimp' differ in leaf color as plants of 'Fiunupfimp' have dark bronze-colored leaves.
2. Plants of the new *Begonia* have larger flowers than plants of 'Fiunupfimp'.
3. Plants of the new *Begonia* have double male flowers whereas plants of 'Fiunupfimp' have single male flowers.
4. Plants of the new *Begonia* and 'Fiunupfimp' differ in flower color as plants of 'Fiunupfimp' have bright orange-colored flowers.

BRIEF DESCRIPTION OF THE PHOTOGRAPH

The accompanying colored photograph illustrates the overall appearance of the new *Begonia* plant showing the colors as true as it is reasonably possible to obtain in colored reproductions of this type. Colors in the photograph may differ slightly from the color values cited in the detailed botanical description which accurately describe the colors of the new *Begonia* plant.

The photograph is a side perspective view of a typical flowering plant of 'Fibegmissmal' grown in a container.

DETAILED BOTANICAL DESCRIPTION

Plants used for the aforementioned photograph and following observations and measurements were grown in 12-cm containers during the summer in a glass-covered greenhouse in Rheinberg, Germany. During the production of the plants, day temperatures ranged from 17° C. to 30° C. and night temperatures ranged from 10° C. to 20° C. Plants were eight weeks old when the photograph and the description were taken. In the following description, color references are made to The Royal Horticultural Society Colour Chart, 2007 Edition, except where general terms of ordinary dictionary significance are used.

Botanical classification: *Begonia hybrida* 'Fibegmissmal'.

Parentage: Naturally-occurring whole plant mutation of *Begonia hybrida* 'Fimissmo', disclosed in U.S. Plant patent application Ser. No. 14/545,695.

Propagation:

*Type*.—By vegetative tip cuttings.

*Time to initiate roots, summer*.—About 18 days at temperatures about 22° C. to 30° C.

*Time to initiate roots, winter*.—About 21 days at temperatures about 22° C. to 30° C.

*Time to produce a rooted young plant, summer*.—About 25 days at temperatures about 22° C. to 30° C.

*Time to produce a rooted young plant, winter*.—About 28 days at temperatures about 20° C. to 25° C.

*Root description*.—Medium in thickness, fibrous; whitish grey in color, actual color of the roots is dependent on substrate composition, water quality, fertilizer type and formulation, substrate temperature and physiological age of roots; plants of the new *Begonia* have not been observed to form tubers.

*Rooting habit*.—Moderately freely branching; medium density.

Plant description:

*Plant form and growth habit*.—Upright to spreading and mounded plant habit; relatively compact; pendulous with development; freely basal branching with about three primary branches; moderately vigorous to vigorous growth habit.

*Plant height*.—About 23 cm.

*Plant width*.—About 34 cm to 46 cm.

*Lateral branch description*.—Length: About 11 cm to 15 cm. Diameter: About 1 cm. Internode length: About 2 cm to 3 cm. Texture: Smooth, glabrous. Color: Close to 182B.

*Leaf description*.—Arrangement: Alternate, simple. Length: About 15 cm to 20 cm. Width: About 7 cm to 11 cm. Shape: Ovate to lanceolate. Apex: Acuminate. Base: Cordate. Margin: Serrate, Texture, upper and lower surfaces: Smooth, glabrous. Venation pattern: Palmate; reticulate. Color: Developing leaves, upper surface: Close to 147A. Developing leaves, lower surface: Close to 184B. Fully expanded leaves, upper surface: Close to 139A; venation, close to 138A. Fully expanded leaves, lower surface: Close to 184B; venation, close to N77D. Petioles: Length: About 8 cm. Diameter: About 4 mm to 6 mm. Texture, upper and lower surfaces: Smooth, glabrous. Color, upper and lower surfaces: Close to 144D.

Flower description:

*Flowering habit*.—Large male double flowers and single female flowers arranged in axillary cymes; freely flowering habit with numerous flowers developing per plant; flowers pendulous and face outwardly to downwardly.

*Fragrance*.—None detected.

*Natural flowering season*.—Plants in full flower about eight weeks after planting; long flowering period, in the garden plants flower freely and continuously throughout the summer in Northern Europe and can be flowered year-round in greenhouses.

*Flower longevity*.—Individual flowers last about four weeks on the plant; flowers persistent.

*Inflorescence height* (*including peduncle*).—About 16 cm to 20 cm.

*Inflorescence diameter*.—About 8 cm to 12 cm.

*Female flower buds*.—Length: About 1.6 cm to 2 cm. Diameter: About 1.2 cm. Shape: Ovoid. Texture: Smooth, glabrous. Color: Close to 49B.

*Female flowers*.—Diameter: About 3.4 cm to 3.6 cm. Depth (height): About 3 cm.

*Female flower tepals*.—Quantity per flower and arrangement: Typically five per flower arranged in a single whorl. Length: About 3 cm. Width: About 2 cm. Shape: Obovate. Apex: Acute. Base: Cuneate. Margin: Entire. Texture, upper and lower surfaces: Smooth, glabrous. Color: When opening, upper surface: Close to 52B. When opening, lower surface: Close to 49B. Fully opened, upper surface: Close to 52A; color does not change with development. When opening, lower surface: Close to 52D; color becoming closer to 52A with development.

*Female flower tepaloids*.—None observed.

*Female flower peduncles*.—Length: About 6 cm to 8 cm. Diameter: About 4 mm. Angle: About 31° to 45° from vertical. Strength: Moderately strong. Texture: Smooth, glabrous. Color: Close to 144D.

*Female flower pedicels*.—Length: About 2 cm to 2.5 cm. Diameter: About 3 mm. Aspect: About 90° from peduncle axis. Strength: Moderately strong. Texture: Smooth, glabrous. Color: Close to 144D.

*Female flowers reproductive organs*.—Quantity of pistils per flower: Six. Pistil length: About 7 mm. Style length: About 7 mm. Style color: Close to N25C. Stigma shape: Curled. Stigma color: Close to 21A. Ovary color: Close to N25C. Fruits and seeds: Fruit and seed development have not been observed on plants of the new *Begonia*.

*Male flower buds*.—Length: About 3.5 cm. Diameter: About 3 cm. Shape: Ovoid. Texture: Smooth, glabrous. Color: Close to 27B.

*Male flowers*.—Diameter: About 9 cm. Depth (height): About 1 cm.

*Male flower tepals*.—Quantity per flower and arrangement: Typically about four or five per flower arranged in a single whorl. Length: About 4.5 cm. Width: About 4.1 cm. Shape: Ovate to oblanceolate. Apex: Acute. Base: Cordate. Margin: Entire. Texture, upper and lower surfaces: Smooth, glabrous.

Color: When opening, upper surface: Close to 49A. When opening, lower surface: Close to 49B. Fully opened, upper and lower surfaces: Close to 41B; color does not change with development.

*Male flower tepaloids*.—Quantity per flower and arrangement: Typically about 18 arranged in multiple whorls. Length: About 3.8 cm. Width: About 2.6 cm. Shape: Oblanceolate. Apex: Obtuse. Base: Cuneate. Margin: Entire. Texture, upper and lower surfaces: Smooth, glabrous. Color: When opening, upper surface: Close to 49A. When opening, lower surface: Close to 49B. Fully opened, upper and lower surfaces: Close to 41B; color does not change with development.

*Male flower peduncles*.—Length: About 9 cm to 11 cm. Diameter: About 4 mm. Angle: About 31° to 45° from vertical. Strength: Moderately strong. Texture: Smooth, glabrous. Color: Close to 144D.

*Male flower pedicels*.—Length: About 2 cm. Diameter: About 2 mm to 3 mm. Aspect: About 90° from peduncle axis. Strength: Moderately strong. Texture: Smooth, glabrous. Color: Close to 144D.

*Male flowers reproductive organs*.—None observed; all transformed into tepaloids.

Pathogen & pest resistance: Resistance to pathogens and pests common to *Begonia* plants has not been observed on plants of the new *Begonia*.

Temperature tolerance: Plants of the new *Begonia* have been observed to tolerate temperatures ranging from about 4° C. to about 35° C.

It is claimed:

1. A new and distinct *Begonia* plant named 'Fibegmissmal' as illustrated and described.

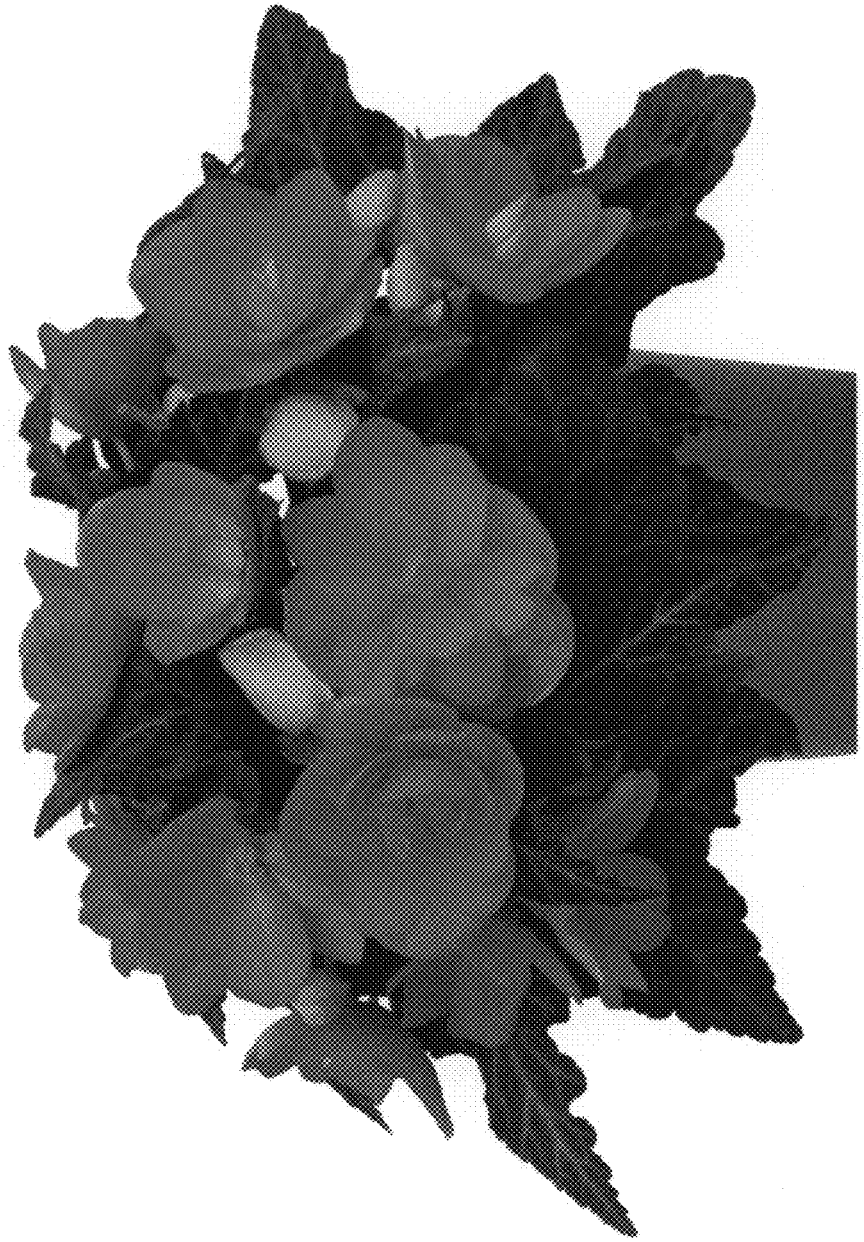

* * * * *